United States Patent
Chen et al.

(10) Patent No.: US 9,250,180 B2
(45) Date of Patent: Feb. 2, 2016

(54) RAMAN SPECTRUM MEASURING METHOD FOR DRUG INSPECTION

(71) Applicants: Nuctech Company Limited, Beijing (CN); Tsinghua University, Beijing (CN)

(72) Inventors: Zhiqiang Chen, Beijing (CN); Li Zhang, Beijing (CN); Jianhong Zhang, Beijing (CN); Hongqiu Wang, Beijing (CN); Ziran Zhao, Beijing (CN); Yumin Yi, Beijing (CN); Jianping Gu, Beijing (CN); Qingping Huang, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 14/495,233

(22) Filed: Sep. 24, 2014

(65) Prior Publication Data
US 2015/0085278 A1   Mar. 26, 2015

(30) Foreign Application Priority Data
Sep. 25, 2013  (CN) .......................... 2013 1 0446679

(51) Int. Cl.
*G01J 3/44* (2006.01)
*G01N 21/47* (2006.01)
*G01N 33/15* (2006.01)
*G01N 21/65* (2006.01)

(52) U.S. Cl.
CPC . *G01N 21/47* (2013.01); *G01J 3/44* (2013.01); *G01N 21/65* (2013.01); *G01N 21/658* (2013.01); *G01N 33/15* (2013.01)

(58) Field of Classification Search
CPC .............. G01J 3/02; G01J 3/44; G01N 21/65; G01N 21/658; G01N 2021/656
USPC .............................................. 356/301, 72–73
See application file for complete search history.

(56) References Cited

U.S. PATENT DOCUMENTS

2008/0221457 A1* 9/2008 Zeng .................... A61B 5/0071
600/477

* cited by examiner

*Primary Examiner* — Abdullahi Nur
(74) *Attorney, Agent, or Firm* — Knobbe, Martens, Olson & Bear, LLP

(57) ABSTRACT

A raman spectrum measuring method for drug inspection is provided, comprising: measuring raman spectrum of a sample to be inspected to acquire an original raman spectrum curve of the sample; determining whether the original raman spectrum curve has a characterizing portion, and if not, measuring a mixture of the sample and an enhancing agent to acquire an enhanced raman spectrum curve of the sample; and if the original raman spectrum curve of the sample to be inspected has a characterizing portion, comparing the original raman spectrum curve of the sample with data in an original raman spectrum database of a drug to determine whether the sample contains the drug, otherwise, comparing the enhanced raman spectrum curve of the sample with data in an enhanced raman spectrum database of the drug to determine whether the sample to be inspected contains the drug.

11 Claims, 3 Drawing Sheets

RAMAN SPECTRUM MEASURING METHOD FOR DRUG INSPECTION

CROSS-REFERENCE TO RELATED APPLICATION

This application claims priorities to Chinese Patent Application Nos. 201310446679.2 filed on Sep. 25, 2013, entitled "Raman spectrum measuring method for drug inspection", in the State Intellectual Property Office of China, the disclosures of which are incorporated herein by reference in their entireties.

BACKGROUND OF THE INVENTION

1. Field of the Invention

The present disclosure relates to a technical field of security inspection, in particular to a method for inspecting drugs using raman spectra technique.

2. Description of the Related Art

At present, Customs Anti-smuggling Bureau typically inspects drugs by selective examination and identification. In the selective examination, reagent kits or test strips are mainly used to test the drugs. The method has advantages of high speed, convenience and low cost. However, it has a strong specificity, e.g., if the type of the sample to be inspected is unknown, it will need to try by various reagents or test strips one by one, in particular, when the smuggling drug is inspected, the test by the reagents or test strips has a poor reliability due to various adulterated compositions contained in the smuggling drugs, and thus may obtain wrong results. The methods based on such as Chromatogram, mass spectrometry are typically used in the identification, however, these methods have complex operations and expensive consumptive materials and thus are difficult to be used in field rapid inspection. Therefore, it needs an easy, rapid, accurate and reliable method to perform the smuggling drug inspection.

SUMMARY OF THE INVENTION

An objective of the present disclosure is to provide a raman spectrum measuring method for drug inspection, which is able to determine rapidly, efficiently and accurately whether the sample to be inspected contains the drug.

In view of this, embodiments of the present invention may be implemented as follows.

In accordance with a first aspect of the present invention, it provides a raman spectrum measuring method for drug inspection, comprising the steps of:

(a) measuring raman spectrum of a sample to be inspected to acquire an original raman spectrum curve of the sample to be inspected;

(b) determining whether the original raman spectrum curve of the sample to be inspected has a characterizing portion or not, and if not, measuring a mixture of the sample to be inspected and an enhancing agent to acquire an enhanced raman spectrum curve of the sample to be inspected; and (c) if the original raman spectrum curve of the sample to be inspected has a characterizing portion, comparing the original raman spectrum curve of the sample to be inspected with data in an original raman spectrum database of a drug to determine whether the sample to be inspected contains the drug, otherwise, if the original raman spectrum curve of the sample to be inspected does not have the characterizing portion, comparing the enhanced raman spectrum curve of the sample to be inspected with data in an enhanced raman spectrum database of a drug to determine whether the sample to be inspected contains the drug.

In an embodiment, the raman spectrum measuring method for drug inspection, before the step (a), further comprises the steps:

(o1) measuring raman spectrum of a drug sample to acquire an original raman spectrum curve of the drug sample;

(o2) determining whether the original raman spectrum curve of the drug sample has the characterizing portion or not, and if the original raman spectrum curve of the drug sample has the characterizing portion, establishing an original raman spectrum database of the drug based on the original raman spectrum curve of the drug sample, otherwise, if the original raman spectrum curve of the drug sample does not have the characterizing portion, measuring a mixture of the drug sample and the enhancing agent to acquire an enhanced raman spectrum curve of the drug sample and establishing the enhanced raman spectrum database of the drug based on the enhanced raman spectrum curve of the drug sample.

In an embodiment, in the step (c), the step of comparing the original raman spectrum curve of the sample to be inspected with data in the original raman spectrum database of the drug is performed by calculating a similarity between the original raman spectrum curve of the sample to be inspected and the original raman spectrum curve of the drug sample, and the step of comparing the enhanced raman spectrum curve of the sample to be inspected with data in the enhanced raman spectrum database of the drug is performed by calculating a similarity between the enhanced raman spectrum curve of the sample to be inspected and the enhanced raman spectrum curve of the drug sample, and if the similarity between the original raman spectrum curve of the sample to be inspected and the original raman spectrum curve of the drug sample is greater than a first threshold or the similarity between the enhanced raman spectrum curve of the sample to be inspected and the enhanced raman spectrum curve of the drug sample is greater than a second threshold, it is determined that the sample to be inspected contains the drug.

In an embodiment, the characterizing portion may be one or more characterizing peak(s) and the similarity is calculated in weight on basis of peak position(s), peak width(s) and/or peak height(s) of the characterizing peak(s).

In an embodiment, the mixture of the sample to be inspected and the enhancing agent may be formed by directly mixing the sample to be inspected with the enhancing agent or mixing the enhancing agent with an aqueous or organic solution of the sample to be inspected, and wherein the mixture of the drug sample and the enhancing agent is formed by directly mixing the drug sample with the enhancing agent or mixing the enhancing agent with an aqueous or organic solution of the drug sample.

In an embodiment, the enhancing agent may contain any one of metal nanoparticles, metal nanolines, metal nanoclusters, carbon nanotubes or carbon nanoparticles having a size in a range of 1-1000 nm, or any combination thereof.

In an embodiment, the enhancing agent may comprise metal nanomaterials.

In an embodiment, the enhancing agent further comprises chloride ions, bromine ions, sodium ions, potassium ions and/or sulfate radical ions.

In an embodiment, the metal comprises any one of gold, silver, copper, magnesium, aluminium, iron, cobalt, nickel, palladium or platinum, or any combination thereof.

DETAILED DESCRIPTION OF THE EMBODIMENTS

Figure 1:
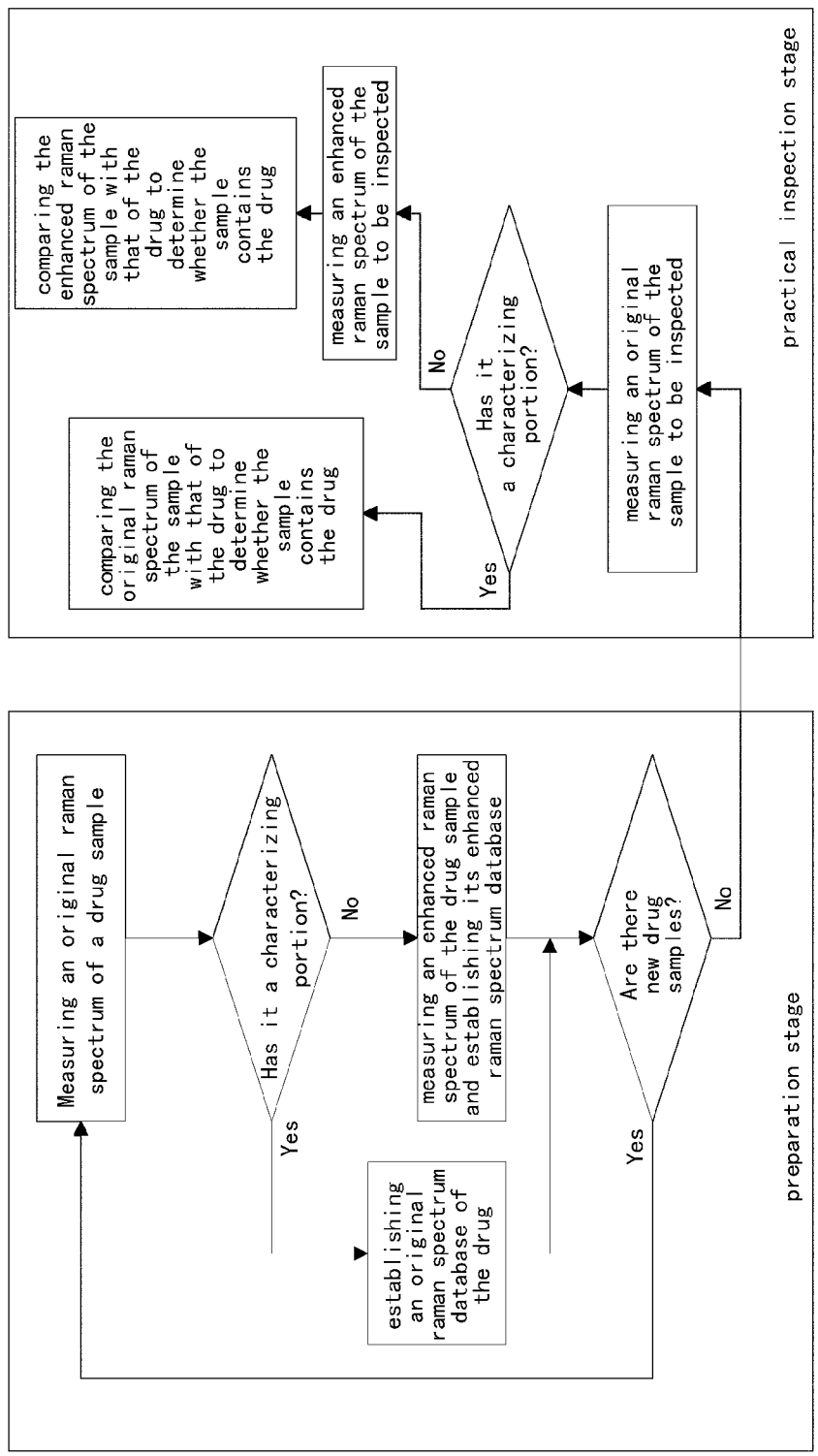
FIG. 1 shows a schematic flow chart of a raman spectrum measuring method for drug inspection in accordance with an embodiment of the present invention.

The specific embodiments of the present invention will be described in detail below with reference to accompanying figures. Throughout the description, identical or similar reference numerals represent identical or similar members. It should be noted that embodiments described herein are depicted only for illustration, instead of limiting to the present invention.

FIG. 1 shows a schematic flow chart of a raman spectrum measuring method for drug inspection in accordance with an embodiment of the present invention. The method may be divided into two stages, i.e., a preparation stage and a practical inspection stage. In the preparation stage, it is intended mainly to establish a raman spectrum database of the drugs to be used in the practical inspection. In the practical inspection stage, the practical sample to be inspected is inspected and is compared with the data of the raman spectrum database of the drug to derive a result.

As an example, the preparation stage may include the following steps of: measuring raman spectrum of a drug sample to acquire an original raman spectrum curve of the drug sample; and determining whether the original raman spectrum curve of the drug sample has a characterizing portion, and if the original raman spectrum curve of the drug sample has the characterizing portion, establishing an original raman spectrum database based on the original raman spectrum curve, otherwise, if the original raman spectrum curve of the drug sample does not have the characterizing portion, measuring a mixture of the drug sample with an enhancing agent to acquire an enhanced raman spectrum curve of the drug sample, and establishing an enhanced raman spectrum database of the drug based on the enhanced raman spectrum curve of the drug sample. The above process may be performed for one or more drug samples respectively until no original or enhanced raman spectra of new drug samples need to be collected.

In some embodiments, the practical inspection stage may include the following steps of: measuring raman spectrum of a sample to be inspected to acquire an original raman spectrum curve of the sample to be inspected; determining whether the original raman spectrum curve of the sample to be inspected has the characterizing portion or not, and if not, measuring a mixture of the sample to be inspected and an enhancing agent to acquire an enhanced raman spectrum curve of the sample to be inspected; and if the original raman spectrum curve of the sample to be inspected has the characterizing portion, comparing the original raman spectrum curve of the sample to be inspected with data in the original raman spectrum database of the drug to determine whether the sample to be inspected contains the drug, otherwise, if the original raman spectrum curve of the sample to be inspected does not have the characterizing portion, comparing the enhanced raman spectrum curve of the sample to be inspected with data in an enhanced raman spectrum database of the drug to determine whether the sample to be inspected contains the drug.

As discussed above, the raman spectrum measuring method for drug inspection in accordance with an embodiment of the present invention inspects the drug by combining the original raman spectrum data and the enhanced raman spectrum data. Such method may optimize the inspection efficiency and the inspection accuracy of the drug as possible as it can. In comparison with typical chemicals, the drug inspection has its special requirement. On one hand, as the drug inspection is often related to identification of criminal behaviours, the drug inspection must be very accurate; on the other hand, as the drug inspection is often performed at exit and entry locations such as airports, customs, the drug inspection must have a very high inspection efficiency and thus some inspection methods that have a high inspection accuracy but have complicated flows are not applied in field rapid inspection while they can be used in further determination in subsequent processes.

For the raman spectrum measuring method for drug inspection, if it only inspects the sample to be inspected directly and performs the determination based on the original raman spectrum data, in some cases, certain drugs may not be inspected correctly, due to the accuracy limit of the inspection. In contrast, if it only inspects the mixture of the sample to be inspected with the enhancing agent and performs the determination based on the enhanced raman spectrum data, it may cause the inspection process to have undesired complexity and reduce the inspection efficiency. As the method according to an embodiment of the present invention uses the combination of the original raman spectrum and the enhanced raman spectrum of the sample to be inspected, it not only ensures the accuracy of the drug inspection, but also improves the inspection efficiency as possible as it can.

In the raman spectrum measuring method for drug inspection according to an embodiment of the present invention, the above preparation stage is optional, for example, the operator may compare the original raman spectrum data or the enhanced raman spectrum data of the known drugs with the inspection results of the practical sample. Further, the above preparation stage may not be performed long before inspecting the practical sample, for example, in order to ensure the accuracy of the inspection or to calibrate the raman spectrum inspection apparatus, it may inspect the drug sample on spot in the field of inspecting the sample to be inspected to acquire the original raman spectrum data or the enhanced raman spectrum data of the drug.

In an example, the step of comparing the original raman spectrum curve of the sample to be inspected with data in the original raman spectrum database of the drug may be performed by calculating a similarity between the original raman spectrum curve of the sample to be inspected and the original raman spectrum curve of the drug sample. As such, the step of comparing the enhanced raman spectrum curve of the sample to be inspected with data in the enhanced raman spectrum database of the drug may be performed by calculating a similarity between the enhanced raman spectrum curve of the sample to be inspected and the enhanced raman spectrum curve of the drug sample.

The similarity may be calculated by several methods, for example, the correlation algorithm, the maximum likelihood algorithm, the absolute value algorithm. For example, if the original raman spectrum curve of the drug is represented by A(x), the original raman spectrum curve of the sample to be inspected is represented by B(x). In an example, with the maximum likelihood algorithm, the similarity between the original raman spectrum curve of the drug and the original raman spectrum curve of the sample to be inspected may be calculated as the equation (1):

$$\mathrm{Corr} = \left(1 - \sqrt{1 - \frac{A(x) \cdot B(x)}{\sqrt{A(x) \cdot A(x)} \sqrt{B(x) \cdot B(x)}}}\right) \times 100\% \qquad (1)$$

where Corr represents the similarity between the original raman spectrum curve of the drug and the original raman spectrum curve of the sample to be inspected and "●" represents dot product operation. In another example, with the correlation algorithm, A(x) and B (x) may be sampled respectively to acquire n sample points respectively, i.e., $A_1$, $A_2, \ldots, A_n$ and $B_1, B_2, \ldots, B_n$. In this way, the similarity Corr between the original raman spectrum curve of the drug and the original raman spectrum curve of the sample to be inspected may be calculated on basis of the equation (2):

$$\mathrm{Corr} = \frac{\left(\left(A(x) - \frac{\sum_{i=1}^{n} A_i}{n}\right) \cdot \left(B(x) - \frac{\sum_{i=1}^{n} B_i}{n}\right)\right)^2}{\left(\left(A(x) - \frac{\sum_{i=1}^{n} A_i}{n}\right) \cdot \left(A(x) - \frac{\sum_{i=1}^{n} A_i}{n}\right)\right) \left(\left(B(x) - \frac{\sum_{i=1}^{n} B_i}{n}\right) \cdot \left(B(x) - \frac{\sum_{i=1}^{n} B_i}{n}\right)\right)} \times 100\% \qquad (2)$$

where "●" represents dot product operation.

In another example, with the absolute value algorithm, A(x) and B (x) may also be sampled respectively to acquire n sample points respectively, i.e., $A_1$, $A_2$, . . . , $A_n$ and $B_1$, $B_2$, . . . , $B_n$. In this way, the similarity Corr between the original raman spectrum curve of the drug and the original raman spectrum curve of the sample to be inspected may be calculated on basis of the equation (3):

$$\mathrm{Corr} = \left(1 - \frac{\sum_{i=1}^{n} |A_i - B_i|}{n}\right) \times 100\% \qquad (3)$$

The above calculation on the similarity may be performed for an entire raman spectrum curve, or may be performed locally for the part in which the characterizing portion is comprised in the raman spectrum curve. The calculation on the similarity between the enhanced raman spectrum curve of the drug and the enhanced raman spectrum curve of the sample to be inspected may be performed in a manner similar to that of the above calculation on the similarity between the original raman spectrum curves of the drug and the sample to be inspected, thus the specific description will be omitted herein. It should be noted that the above paragraphs only provide some examples of calculating the similarity, and other methods for calculating the similarity that are known by the skilled person in the art may also be used.

For the similarity between the original raman spectrum curve of the sample to be inspected and the original raman spectrum curve of the drug sample, if it is greater than a first threshold, it is determined that the sample to be inspected contains the drug. As such, if the similarity between the enhanced raman spectrum curve of the sample to be inspected and the enhanced raman spectrum curve of the drug sample is greater than a second threshold, it is determined that the sample to be inspected contains the drug. The first threshold and the second threshold may be equal or not equal. The first and second thresholds may be set on basis of the factors such as practical inspection requirement, accuracy of the inspection instrument.

In the embodiments of the present invention, the term of "characterizing portion" means a critical portion of a raman spectrum curve of a certain drug or a sample to be inspected so that the raman spectrum curve is distinguished from those of other drugs or samples to be inspected. For example, the characterizing portion may be one or more characterizing peak(s), characterizing valley(s), inflection points of phase.

In the case that the original raman spectrum curve of the drug includes the characterizing peak(s), the above similarities may be calculated in weight on basis of peak position(s), peak width(s) and/or peak height(s) of the characterizing peak(s). In an example, before the similarity is calculated, the characterizing peak(s) may be searched and sequenced. In the case that the characterizing peaks of the original raman spectrum curve or the enhanced raman spectrum curve of the drug are relatively noticeable, the calculation on the similarity in practice may even be simplified as determining the similarity directly by searching whether the original raman spectrum curve or the enhanced raman spectrum curve of the sample to be inspected includes the characterizing peak(s) corresponding to the characterizing peak(s) of the original raman spectrum curve or the enhanced raman spectrum curve of the drug at one or more positions, or not.

In an example, when the inspection is performed on basis of the enhanced raman spectrum data of the drug, the mixture of the sample to be inspected and the enhancing agent may be formed by directly mixing the sample to be inspected with the enhancing agent or mixing the enhancing agent with an aqueous or organic solution of the sample to be inspected. As such, the mixture of the drug sample and the enhancing agent is formed by directly mixing the drug sample with the enhancing agent or mixing the enhancing agent with an aqueous or organic solution of the drug sample. As an example, the enhancing agent may contain any one of metal nanoparticles, metal nanolines, metal nanoclusters, carbon nanotubes or carbon nanoparticles having a size in a range of 1-1000 nm or any combination thereof. In another example, the enhancing agent may include metal nanomaterials. The enhancing agent may further comprise chloride ions, bromine ions, sodium ions, potassium ions and/or sulfate radical ions besides the metal nanomaterial. For example, the metal may includes any one of gold, silver, copper, magnesium, aluminium, iron, cobalt, nickel, palladium or platinum or any combination thereof. In the mixture of the drug sample and the enhancing agent, molecules of the drug may be attached to the surface of the enhancing agent material and an electromagnetic field of the surface of the enhancing agent material may enhance the raman spectrum signal of the drug sample.

The raman spectrum data may be acquired by directing a light emitted from a laser onto the drug sample or the sample to be inspected and extracting the raman scattering light produced by the drug sample or the sample to be inspected under laser irradiation and performing the spectrum analysis to derive the raman spectrum curve.

Figure 2:
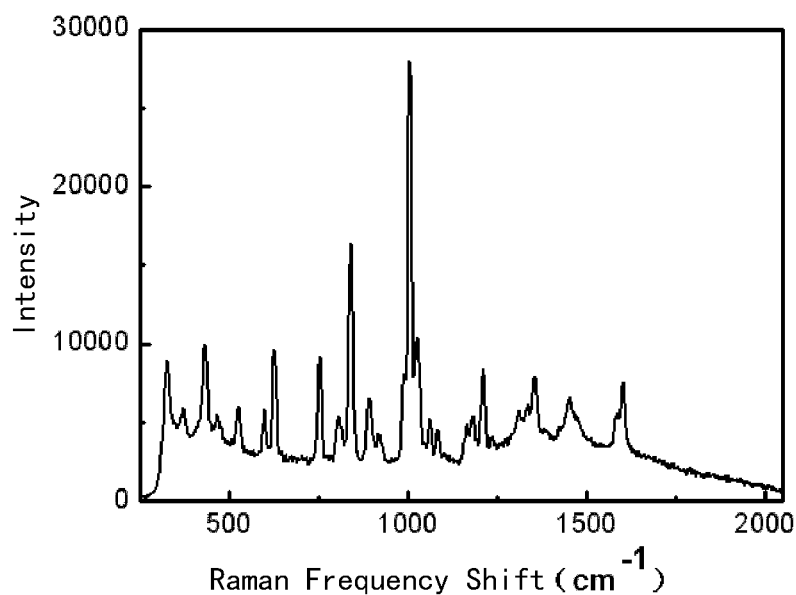
FIG. 2 is a schematic view showing an original raman spectrum curve of first drug inspected by the raman spectrum measuring method for drug inspection in accordance with an embodiment of the present invention.
Figure 3A:
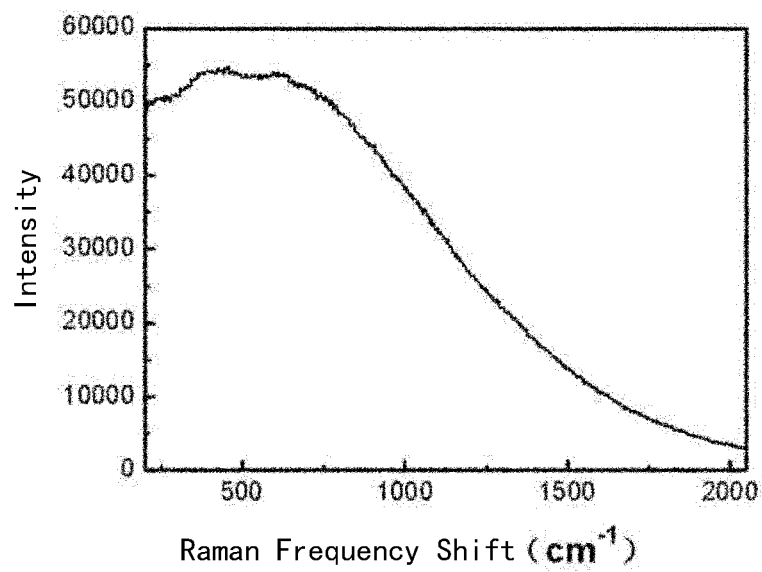
FIG. 3a is a schematic view showing an original raman spectrum curve of second drug inspected by the raman spectrum measuring method for drug inspection in accordance with an embodiment of the present invention.
Figure 3B:
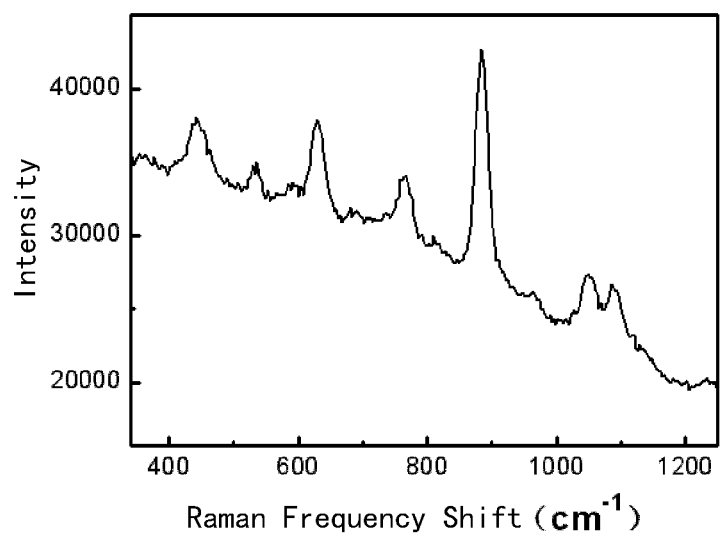
FIG. 3b is a schematic view showing an enhanced raman spectrum curve of the second drug inspected by the raman spectrum measuring method for drug inspection in accordance with an embodiment of the present invention.

FIGS. 2, 3a and 3b provide examples of inspecting the drug by the raman spectrum measuring method according to an embodiment of the present invention. FIG. 2 shows the original raman spectrum curve of a first drug. It can be seen from FIG. 2 that the original raman spectrum curve of the first drug includes significant or noticeable characterizing peaks at near 850 cm$^{-1}$ and near 1000 cm$^{-1}$. For the inspection of such drug, it only needs to acquire the original raman spectrum curve of the sample to be inspected and to compare it with the original raman spectrum curve of the drug without using the enhanced raman spectrum data.

FIGS. 3a and 3b show the original raman spectrum curve and the enhanced raman spectrum curve of a second drug respectively. Seen from FIG. 3a, the original raman spectrum curve of the second drug has no significant or noticeable characterizing peak(s). Thus, if the inspection is performed directly on basis of the original raman spectrum data, the inspection may be not performed correctly. Further, the enhanced raman spectrum curve of the second drug acquired from the mixture of the aqueous or organic solution(obtained by solving the second drug sample into the water or organic solvent) of the second drug sample with the enhancing agent has significant or noticeable characterizing peak(s), as illustrated in FIG. 3b. The enhanced raman spectrum curve of the second drug has significant or noticeable characterizing peak(s) at near 530 cm$^{-1}$ and near 630 cm$^{-1}$. It should be noted that not all of peaks in the enhanced raman spectrum are the characterizing peak(s). For example, in FIG. 3b, the peaks other than those at near 530 cm$^{-1}$ and near 630 cm$^{-1}$ are not the characterizing peaks, e.g. but may be produced by the enhancing agent or the solvent, and thus they cannot represent characteristics of the drug. Therefore, in the inspection of the second drug, the enhanced raman spectrum curve of the sample to be inspected should be measured and collected and be compared with the enhanced raman spectrum curve of the drug to determine whether the sample to be inspected contains the second drug.

Although the present invention has been explained with reference to the drawings, the embodiments shown in the drawings are only illustrative, instead of limiting the present invention.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What the claims is:

1. A raman spectrum measuring method for drug inspection, comprising the steps of:
   (a) measuring raman spectrum of a sample to be inspected to acquire an original raman spectrum curve of the sample to be inspected;
   (b) determining whether the original raman spectrum curve of the sample to be inspected has a characterizing portion or not, and if not, measuring a mixture of the sample to be inspected and an enhancing agent to acquire an enhanced raman spectrum curve of the sample to be inspected; and
   (c) if the original raman spectrum curve of the sample to be inspected has a characterizing portion, comparing the original raman spectrum curve of the sample to be inspected with data in an original raman spectrum database of a drug to determine whether the sample to be inspected contains the drug, otherwise, if the original raman spectrum curve of the sample to be inspected does not have the characterizing portion, comparing the enhanced raman spectrum curve of the sample to be inspected with data in an enhanced raman spectrum database of a drug to determine whether the sample to be inspected contains the drug.

2. The raman spectrum measuring method for drug inspection of claim 1, further comprising before step (a), the steps:
   (o1) measuring raman spectrum of a drug sample to acquire an original raman spectrum curve of the drug sample;
   (o2) determining whether the original raman spectrum curve of the drug sample has the characterizing portion or not, and if the original raman spectrum curve of the drug sample has the characterizing portion, establishing an original raman spectrum database of the drug based on the original raman spectrum curve of the drug sample, otherwise, if the original raman spectrum curve of the drug sample does not have the characterizing portion, measuring a mixture of the drug sample and the enhancing agent to acquire an enhanced raman spectrum curve of the drug sample and establishing the enhanced raman spectrum database of the drug based on the enhanced raman spectrum curve of the drug sample.

3. The raman spectrum measuring method for drug inspection of claim 1, wherein, in step (c), the step of comparing the original raman spectrum curve of the sample to be inspected with data in the original raman spectrum database of the drug is performed by calculating a similarity between the original raman spectrum curve of the sample to be inspected and the original raman spectrum curve of the drug sample, and the step of comparing the enhanced raman spectrum curve of the sample to be inspected with data in the enhanced raman spectrum database of the drug is performed by calculating a similarity between the enhanced raman spectrum curve of the sample to be inspected and the enhanced raman spectrum curve of the drug sample, and if the similarity between the original raman spectrum curve of the sample to be inspected and the original raman spectrum curve of the drug sample is greater than a first threshold or the similarity between the enhanced raman spectrum curve of the sample to be inspected and the enhanced raman spectrum curve of the drug sample is greater than a second threshold, it is determined that the sample to be inspected contains the drug.

4. The raman spectrum measuring method for drug inspection of claim 3, wherein a characterizing portion of the raman spectrum curves is one or more characterizing peak(s) and the similarity is calculated in weight on basis of peak position(s), peak width(s) and/or peak height(s) of the characterizing peak(s).

5. The raman spectrum measuring method for drug inspection of claim 1, wherein the mixture of the sample to be inspected and the enhancing agent is formed by directly mixing the sample to be inspected with the enhancing agent or mixing the enhancing agent with an aqueous or organic solution of the sample to be inspected, and wherein the mixture of the drug sample and the enhancing agent is formed by directly mixing the drug sample with the enhancing agent or mixing the enhancing agent with an aqueous or organic solution of the drug sample.

6. The raman spectrum measuring method for drug inspection of claim 1, wherein the enhancing agent contains any one of metal nanoparticles, metal nanolines, metal nanoclusters, carbon nanotubes or carbon nanoparticles having a size in a range of 1-1000 nm or any combination thereof.

7. The raman spectrum measuring method for drug inspection of claim 1, wherein the enhancing agent comprises metal nanomaterials.

8. The raman spectrum measuring method for drug inspection of claim 7, wherein the enhancing agent further comprises chloride ions, bromine ions, sodium ions, potassium ions and/or sulfate radical ions.

9. The raman spectrum measuring method for drug inspection of claim 6, wherein the metal comprises any one of gold, silver, copper, magnesium, aluminium, iron, cobalt, nickel, palladium or platinum, or any combination thereof.

10. The raman spectrum measuring method for drug inspection of claim 7, wherein the metal comprises any one of gold, silver, copper, magnesium, aluminium, iron, cobalt, nickel, palladium or platinum, or any combination thereof.

11. The raman spectrum measuring method for drug inspection of claim 8, wherein the metal comprises any one of gold, silver, copper, magnesium, aluminium, iron, cobalt, nickel, palladium or platinum, or any combination thereof.

* * * * *